United States Patent [19]

Feola et al.

[11] Patent Number: 5,521,136
[45] Date of Patent: May 28, 1996

[54] PROCESS FOR THE PREPARATION OF ORGANOTITANIUM COMPOUNDS AND THEIR USE IN CATHODICALLY DEPOSITABLE ELECTRODEPOSITION COATING MATERIALS

[75] Inventors: Roland Feola; Willibald Paar; Johann Gmoser, all of Graz, Austria

[73] Assignee: Vianova Kunstharz, A.G., Graz, Austria

[21] Appl. No.: 294,863

[22] Filed: Aug. 29, 1994

[30] Foreign Application Priority Data

Aug. 27, 1993 [AT] Austria ................................. 1721/93

[51] Int. Cl.⁶ ............................................... B01J 31/00
[52] U.S. Cl. .................................... 502/152; 502/156
[58] Field of Search .................................. 502/152, 156

[56] References Cited

U.S. PATENT DOCUMENTS

| | | | |
|---|---|---|---|
| 4,431,781 | 2/1984 | Paar | 525/502 |
| 4,568,709 | 2/1986 | Paar et al. | 523/414 |
| 4,617,408 | 10/1986 | Nestler et al. | 502/156 |
| 4,788,234 | 11/1988 | Schipfev et al. | 523/402 |
| 4,845,170 | 7/1989 | Paar et al. | 525/452 |
| 4,942,196 | 7/1990 | Paar et al. | 524/327 |
| 4,973,613 | 11/1990 | Paar | 523/404 |
| 4,994,507 | 2/1991 | Debroy et al. | 502/152 |
| 5,132,341 | 7/1992 | Paar | 523/404 |

*Primary Examiner*—Sharon Gibson
*Attorney, Agent, or Firm*—Breiner & Breiner

[57] ABSTRACT

A process for the preparation of organotitanium compounds and to their use as crosslinking catalysts in cathodically depositable electro-deposition coating materials is described. The organotitanium compounds are obtained by first carrying out partial transesterification of tetraalkyl orthotitanates with alkylene glycols which are capable of forming chelates, and then completing the transesterification of the resulting intermediate with hydroxyl compounds based on modified mono- and/or diepoxide compounds.

Cathodically depositable electrodeposition coating materials which contain the organotitanium compounds prepared in accordance with the invention provide, after curing in a temperature range from 160° to 180° C., coating films having excellent stability and the like properties, without the need to use additional crosslinking catalysts based on heavy metals such as lead or tin.

8 Claims, No Drawings

PROCESS FOR THE PREPARATION OF ORGANOTITANIUM COMPOUNDS AND THEIR USE IN CATHODICALLY DEPOSITABLE ELECTRODEPOSITION COATING MATERIALS

FIELD OF INVENTION

The present invention relates to a process for the preparation of organotitanium compounds and to their us as cross-linking catalysts in cathodically depositable electrodeposition coating materials. The organotitanium compounds are obtained by first carrying out partial transesterfication of tetraalkyl orthotitanates with alkylene glycols which are capable of forming chelates and then completing the transesterification of the resulting intermediate with hydroxyl compounds based on modified mono- and/or diepoxide compounds.

BACKGROUND INVENTION

The use of organotitanium compounds as crosslinking catalysts in cathodically depositable electrodeposition coating materials has been recommended for many years. For example, DE-A 27 52 198 describes organic titanium compounds which are in the form of chelates and which, in addition, can be reacted at least in part with cationic coating binders. The products obtained are not suited to practical application. Thus, simple organotitanium compounds such as tetraalkyl orthotitanates can only be dispersed in an aqueous medium with great difficulties, using wetting agents, and are not stable to hydrolysis. Water-soluble chelate compounds of low molecular weight, in the course of the conventional methods of ultrafiltration, are uncontrollably removed from the deposition coating material. Moreover, the obtained products of reaction of such organotitanium compounds with cationic coating binders are similarly not stable to hydrolysis.

Proposals for overcoming the above described difficulties are set forth in AT Patent 392 647 U.S. Pat. No. 4,973,613 corresponding to and in AT Patent 390 451 corresponding to U.S. Pat. No. 4,973,613, which relate to titanium chelate compounds of β-hydroxyalkylamine compounds, preferably having a relatively high molecular mass. The ability to use these products for combinations with cationic coating binders, however, are severely limited, since they lead to the development of a pronounced structural viscosity.

U.S. Pat. No. 5,132,341 corresponding to AT Patent 393 510 corresponding to U.S. Pat. No. 5,132,341, describes titanium-containing epoxy resin-amine adducts as pigment paste resins for cathodically depositable coating binders. However, "aging," for example in the case of too little of the coating material being used in the deposition tank, results in hydrolysis products which cause a settling of the pigments, surface defects in the deposited films, and a reduced reactivity of the catalyst component restricting their use.

The titanium phenolates obtained in accordance with AT Patent 390 621 corresponding to U.S. Pat. No. 4,942,196 are more stable to hydrolysis. However, these products cause severe discoloration of the baked films, as a result of which it is impossible to use the products in many applications, for example in light-colored primers.

Moreover, all of the known organotitanium compounds require, for their processing, considerable quantities of organic auxiliary solvents, which cause environmental problems and therefore their use is not favored.

AT Patent 396 373 describes a process for the preparation of organotitanium compounds which are stable to hydrolysis, which contain small proportions of organic auxiliary solvents and are based on alkylation products of phenols, modified with glycidyl compounds. However, such products also have a negative effect on the stability on storage of pigment pastes. The viscosity behavior of these pigment pastes is anomalous, i.e., at relatively high solids content their viscosity rises rapidly (thickening of the pigment pastes) while at a lower solids content the pigments tend increasingly to settle.

It has now been found that the demand for pigment pastes which are free of heavy metals, stable on storage and ready for use in the so-called two-component process can be met if the cross-linking catalysts used in cathodically depositable electrodeposition coating materials are organotitanium compounds which are obtained by a two-stage transesterification of tetraalkyl orthotitanates using specially selected hydroxyl compounds.

SUMMARY OF INVENTION

The present invention relates to a process for the preparation of organotitanium compounds which is characterized in that (A) 1.0 mol of tetraalkyl orthotitanate is transesterified with (B) 2.0 mol of an alkylene glycol which is capable of forming chelates, the reaction being carried out to 50% of the theoretical conversion of component (A) with the elimination of the corresponding quantity of alcohol, and subsequently the resulting intermediate (AB) is transesterified completely with (C) from 0.5 to 1.0 mol of a compound which contains at least two hydroxyl groups and is based on a modified mono- or diepoxide compound, with elimination of the remaining quantity of alcohol.

The invention further relates to the use of the titanium compounds prepared in this way, in particular in mixtures with pigment pastes, as crosslinking catalysts in cathodically depositable electrodeposition coating materials.

Cathodically depositable electrodeposition coating materials which contain the organotitanium compounds prepared in accordance with the present invention give rise, after curing in a temperature range of from 160° to 180° C., to coating films having properties as required by the users, without the need to make additional use of crosslinking catalysts based on heavy metals such as lead or tin.

In addition to the hydrophobic segments of the molecules, which are derived from the alkylene glycols and the epoxide compounds, the disclosed organotitanium compounds also contain free and/or chelated hydroxyl groups, which have a favorable effect on the stability, in particular, of the mixtures of the organotitanium compounds with pigment pastes.

The tetraalkyl orthotitanates used as component (A) are available commercially with those containing isopropyl or butyl radicals being preferred. The alkylene glycols employed as component (B) must form a chelate with the titanium atom. In this context see Ullmanns Enzyklopädie der technischen Chemie [Ullmann's Encyclopedia of Industrial Chemistry], 4th edition, volume 23, page 287 ff., Verlag Chemie, 1983). In such alkylene glycols the hydroxyl groups are in an α,γ-configuration with respect to one another, enabling the formation of a stable 6-atom ring structure. Illustrative Glycols are 2,2,4-trimethyl-1,3-pentanediol, 1,3-butanediol, 2,2-dimethyl-1,3-propanediol (neopentylglycol) and 2-ethyl-2-butyl-1,3-propanediol. Preferably, use is made of 2-methyl-2,4-pentanediol (hexylene glycol) and 2-ethyl-1,3-hexanediol (octylene glycol). Component (C) as disclosed herein is a compound which contains at least two hydroxyl groups and is based on modified mono- and/or diepoxide compounds. For the preparation of products in accordance with component (C), commercially available aliphatic and/or aromatic mono- and/or diepoxide compounds are reacted with primary and/or secondary monoamines and/or diamines and/or primary-tertiary diamines and/or alkanolamines. It is also possible to use ethers of bisphenol A-diepoxy resins with monoalcohols, modified if desired with diamines, as component (C).

The preparation of the organic titanium compounds is carried out in two stages of reaction. In the first stage 1.0 mol of component (A) is partially transesterified with 2.0 mol of component (B), the reaction being carried out to 50% of the theoretical conversion of component (A), with the elimination of the corresponding quantity of alcohol. The resulting intermediate (AB) is transesterified completely using from 0.5 to 1.0 mol of component (C), with the elimination of the remaining quantity of alcohol.

The organotitanium compounds prepared in accordance with the invention contain protonatable groups and can be added in concentrated form to the coating binder or, preferably, to a pigment paste, protonation being carried out, if desired, together with the binder. However, they can also be added to the coating material in a neutralized form diluted with water and/or auxiliary solvents.

Suitable cationic coating binders whose crosslinking reactions by transesterification, transurethanization or the reaction of terminal double bonds can be catalyzed using the organotitanium compounds prepared in accordance with the invention are known in large numbers from the literature. A more detailed discussion of the structure and chemistry of these products is therefore unnecessary.

The organotitanium compounds are fully compatible with the coating binders under cold conditions. They remain in the resin phase of the diluted coating material, and thus in the deposited film.

The cathodically depositable electrodeposition coating materials, whose preparation and performance testing is carried out by methods familiar to the person skilled in the art, contain from 0.2 to 2.0% by weight, preferably from 0.3 to 1.5% by weight, of titanium, based on the overall solids content of the binders.

DETAILED AND PRESENTLY PREFERRED EMBODIMENTS

The following examples illustrate the invention without limiting its scope. All parts and percentages relate to units by weight, unless otherwise indicated.

The abbreviation EEW denotes epoxide equivalent weight, i.e., the quantity (in grams) of an epoxy resin which contains one epoxide group.

1. Components (C1) to (C3)

(C1): reaction product of 950 g (1 mol) of an epoxy resin based on bisphenol A and epichlorohydrin (EEW about 475) with 210 g (2 mol) of diethanolamine (MW 1160).

(C2): reaction product of 500 g (2 mol) of Cardura® E which is a glycidyl ester of $C_9$–$C_{11}$-monocarboxylic acids, having an EEW of about 250 with 104 g (1 mol) of aminoethylethanolamine (MW 640).

(C3): reaction product of 760 g (2 mol) of an epoxy resin based on bisphenol A and epichlorohydrin (EEW about 190) with 260 g (2 mol) of 2-ethylhexanol and 130 g (1 mol) of diethylaminopropylamine (MW 1150).

2. Preparation of the Organotitanium Compounds (TI1) to (TI6)

EXAMPLES 1 TO 6

Example 1

In an appropriate reaction vessel, 340 g of tetra-n-butyl orthotitanate (1.0 mol) and 236 g of hexylene glycol (2.0 mol) are heated to 60°–70° C., and 148 g of n-butanol (2 mol) are removed in vacuo with vigorous stirring. The reaction mixture is cooled to about 25° C. and then 580 g (0.5 mol) of component (C1) are added. The mixture is heated to 120° C. with stirring. A further 148 g of n-butanol (2 mol) are removed in vacuo.

Organotitanium compounds are prepared analogously in accordance with the information in Table 1.

TABLE 1

| EXAMPLE | COMPONENT (A) (MOL) | COMPONENT (B) (MOL) | COMPONENT (C) (MOL) | TITANIUM CONTENT[1] |
|---|---|---|---|---|
| 1 (TI1) | BuTi (1.0) | Hex (2.0) | C1 (0.5) | 5.6% |
| 2 (TI2) | BuTi (1.0) | Hex (2.0) | C3 (1.0) | 3.3% |
| 3 (TI3) | BuTi (1.0) | Hex (2.0) | C2 (1.0) | 5.2% |
| 4 (TI4) | BuTi (1.0) | Oct (2.0) | C1 (0.5) | 5.2% |
| 5 (TI5) | BuTi (1.0) | Oct (2.0) | C3 (0.5) | 5.3% |
| 6 (TI6) | BuTi (1.0) | Hex (2.0) | C2 (0.75) | 6.3% |

[1] based on solids content
BuTi: Tetra-n-butyl orthotitanate (MW 340)
Hex: Hexylene glycol (2-methyl-2,4-pentanediol) (MW 118)
Oct: Octylene glycol (2-ethyl-1,3-hexanediol) (MW 146)

3. Preparation of the Organotitanium Compound (TIC) as Comparative Example According to AT Patent 396 373

Example 1

In an appropriate reaction vessel, 220 g of 4-nonylphenol (1 mol) with 130 g of 2-diethylaminopropylamine (1 mol) and 100 g of toluene are heated to 75° C., and then 33 g of 91% paraformaldehyde (1 mol) are added with gentle cooling. The temperature is slowly raised until a steady azeotropic distillation is established. 21 g of water of reaction are separated off and then the mixture is cooled to 60° C. 200 g of a diepoxy resin based on polypropylene glycol (EEW about 200) are added. The temperature is raised to 80° C. and maintained at this level until the epoxide value has reached virtually zero. Subsequently 186 g of 2-ethylhexyl monoglycidyl ether (1 mol) are added. The mixture is maintained at from 85° to 100° C. once more until the epoxide value has reached virtually zero. The toluene is distilled off in vacuo. Following the addition of 170 g of tetra-n-butyl orthotitanate (0.5 mol), the mixture is stirred at 90° C. for 30 minutes before the temperature is raised to 120° C. and the butanol formed (74 g≈1 mol) is removed in vacuo. The resulting product has a titanium content of 3.1% (metal, based on the solids content). The product is diluted to 70% using a mixture of water and formic acid (40 mmol of formic acid per 100 g of solid resin).

4. Preparation of the Binders (BM1) and (BM2) Employed in the Cathodically Depositable Electrodeposition Coating Materials

4.1 Binder (BM1) According to EP 0 158 128 B1 Corresponding to U.S. Pat. No. 4,568,709

Example 6

In the presence of 0.5 g of diphenylparaphenylenediamine (inhibitor), 700 g of B 180**) are reacted with 100 g of maleic anhydride in a known manner, at 200° C., until the latter has become completely reacted. After cooling to 100° C., 130 g of 2-ethylhexanol are added and esterification is carried out at 120° C. until the theoretical acid number of the monoester is reached.

**) B 180 is a liquid polybutadiene oil (about 75% of 1,4-cis, about 24% of 1,4-trans and about 1% of vinyl double bonds; molecular weight about 1500±15%; iodine number about 450 g/100 g).

110 g of monoester (corresponding to about 0.12 mol of COCH groups) are reacted with 212 g of a bisphenol A-diepoxy resin (EEW about 190) in 80% solution in diethylene glycol dimethyl ether, at 120° C., until the acid number is virtually zero. After the addition of 108 g of diethylene glycol dimethyl ether, 59 g of diethylaminopropylamine (0.45 mol) and 59 g of 2-ethylhexylamine (0.45 mol), the mixture is reacted at from 65° to 70° C. until the epoxide value is virtually zero. When this value has been reached, 114 g of bisphenol A (0.5 mol) and 50 g of 91% paraformaldehyde (1.5 mol) are added. The reaction is continued at 60° C. until the content of free formaldehyde reaches from 0.5 to 1%. The solids content is 77%.

4.2 Binder (BM2) According to EP 0 209 857 B1 Corresponding to U.S. Pat. No. 4,845,170

Example 1

In an appropriate reaction vessel, 220 g of nonylphenol (1 mol) with 130 g of diethylaminopropylamine (1 mol) and 100 g of toluene are heated to 75° C., and then 33 g of 91% paraformaldehyde (1 mol) are added to the mixture with gentle cooling. The temperature is raised slowly until a steady azeotropic distillation is established. After 21 parts of water of reaction have been separated off, the toluene is removed in vacuo and the product is dissolved in 167 parts of diethylene glycol dimethyl ether.

304 g (1.0 mol) of a tolylene diisocyanate semiblocked with 2-ethylhexanol are added to the resulting solution at from 30° to 40° C. with cooling. The temperature of 40° C. is maintained for 1.5 hours until the NCO value is virtually zero.

Subsequently, 475 g of an epoxy resin based on bisphenol A and epichlorohydrin (EEW about 475) are dissolved in 200 g of propylene glycol monomethyl ether and, after 835 g of the precursor prepared above have been added, the mixture is reacted at from 95° to 100° C. until the epoxide value is virtually zero. The solids content is 70%.

5. Preparation of the Pigment Paste Resin (PP1) Employed in the Cathodically Depositable Electrodeposition Coating Materials

5.1 Pigment Paste Resin (PH1) According to EP 0 158 128 B1 Corresponding to U.S. Pat. No. 4,568,709, Based on an Oxazolidine-Modified Epoxy Resin According to EP 0 076 955 B1 Corresponding to U.S. Pat. No. 4,431,781

500 g of an epoxy resin based on bisphenol A and epichlorohydrin (EEW about 500) are dissolved in 214 g of propylene glycol monomethyl ether and are reacted at 110° C. with 83 g of a monoester of phthalic anhydride and 2-ethylhexanol, in the presence of 0.5 g triethylamine as catalyst, until the acid number is less than 3 mg of KOH/g. Then 120 g of an NH-functional oxazolidine from aminoethylethanolamine, 2-ethylhexyl acrylate and formaldehyde, and 26 g of diethylaminopropylamine are added. The mixture is reacted at 80° C. until the epoxide value is virtually zero and is diluted to a solids content of 64% with 200 g of propylene glycol monomethyl ether.

6. Testing of the Organic Titanium Compounds (TI1) to (TI6) in Comparison with (TIC) as Crosslinking Catalysts in Cathodically Depositable Electrodeposition Coating Materials

6.1 Preparation of Paints 1 to 8

| | |
|---|---|
| 1,562 | Pigment paste resin (PH1), 64% |
| 40 | Color black |
| 4,960 | Titanium dioxide |
| 92 | 5 N formic acid |
| 3,346 | Deionized water |
| 10,000 | Pigment paste, 60% |

Subsequently, the quantities of titanium compounds TI1 to TI6 and TIC corresponding to Table 2 are stirred into the pigment paste.

Using 90 parts of the cationic binder (BMI) or (BM2) and 60 parts of the pigment paste (based in each case on the solids content and without taking into account the quantity of titanium compound added), paints having a pigment/binder ratio of 0.5:1 are prepared under conditions conforming to those encountered in practice.

TABLE 2

(the quantities indicated are based in each case on the solids content)

| PAINT | BINDER COMBINATION 90/10 | TITANIUM COMPOUND PARTS PER 100 BM | % TITANIUM[1] |
|---|---|---|---|
| 1 | BM1/PH1 | TI2 15 | 0.43 |
| 2 | BM2/PH1 | TI1 20 | 0.93 |
| 3 | BM2/PH1 | TI3 30 | 1.20 |
| 4 | BM1/PH1 | TI4 12 | 0.56 |
| 5 | BM1/PH1 | TI5 18 | 0.81 |
| 6 | BM2/PH1 | TI6 5 | 0.30 |
| 7 | BM1/PH1 | TIC 20 | 0.52 |
| 8 | BM2/PH1 | TIC 15 | 0.40 |

[1]Titanium content based on the overall solids content of the paint binders

6.2. Testing of the Storability of Pigment Pastes

After a storage time of four weeks at room temperature, pigment pastes having a viscosity of 5000–8000 m. Pas*), highly suitable for practical use, and containing the organic titanium compounds TI1 to TI6 show no noticeable changes.

After a storage time of one week, the two pigment pastes containing the titanium compound TIC exhibit, in the same viscosity range, a severe thixotropy (thickening). If the pigment pastes are diluted with water to a viscosity of about 2000–4000 m. Pas*), then after a storage time of only 5 days this leads to the partial "separation" or settling of the pigments.

*) measured according to ASTM D 2196/86 (Brookfield rotary viscometer 10 rpm/spindle 3, 23° C.)

6.3. Assessment of the Paint Films Deposited and then Baked

The batches prepared according to 6.1 are adjusted to a solids content of 18% using deionized water.

After a homogenization period of 24 hours, the paints are cathodically deposited on cleaned, nonphosphatized steel panels. The deposition conditions are chosen such that the films have a dry film thickness of 22±2 μm. Curing is carried out by baking in a circulating-air oven (20 min/180° C.).

All of the coatings display excellent mechanical properties (impact test according to ASTM-D-2794-90: at least 80 i.p.; no flaking in the mandrel bending test according to ASTM D-522-88) and excellent corrosion resistance (salt spray test according to ASTM B 117-90 after a test period of 360 hours: max. 2 mm).

As will be apparent to one skilled in the art, various modification can be made within the scope of the aforesaid description. Such modifications being within the ability of one skilled in the art form a part of the present invention and are embraced by the appended claims.

It is claimed:

1. Process for the preparation of organotitanium compounds, comprising (A) 1.0 mol of a tetraalkyl orthotitanate is transesterified with (B) 2.0 mol of an alkylene glycol having hydroxyl groups in an $\alpha,\gamma$-configuration with respect to one another and which is capable of forming chelates, the reaction being carried out to 50% of the theoretical conversion of component (A) with the elimination of the corresponding quantity of alcohol, and subsequently the resulting intermediate (AB) is transesterified completely with (C) from 0.5 to 1.0 mol of a compound which contains at least two hydroxyl groups and is based on a modified mono- or diepoxide compound, with elimination of the remaining quantity of alcohol.

2. Process according to claim 1, wherein 2-methyl- 2,4-pentanediol or 2-ethyl-1,3-hexandediol is employed as component (B).

3. Process according to claims 1 or 2, wherein ethers of bisphenol A-diepoxy resins with monoalcohols, optionally modified with diamines, are employed as component (C).

4. Organotitanium compounds prepared according to claims 1, 2 or 3, as a crosslinking catalyst in combination with a cathodically depositable electrodeposition coating material, wherein the titanium content, based on the overall solids content of the coating binders, is from 0.2 to 2.0% by weight.

5. The combination of claim 4 wherein the titanium content is from 0.3 to 1.5% by weight.

6. The combination of claims 4 or 5 further including a pigment paste.

7. Process according to claims 1 or 2, wherein the reaction products of aliphatic or aromatic mono- or diepoxide compounds with primary or secondary monoamines or diamines or primary tertiary diamines or alkanolamines are employed as component (C).

8. Process according to claims 1 or 2, wherein the reaction products of aliphatic and aromatic mono- and diepoxide compounds with primary and secondary monoamines and diamines and primary tertiary diamines and alkanolamines are employed as component (C).

* * * * *